United States Patent [19]

Singh et al.

[11] Patent Number: 4,906,563

[45] Date of Patent: Mar. 6, 1990

[54] DETECTION OF SKATOLE FOR MEAT QUALITY

[75] Inventors: Prithipal Singh, Los Altos Hills; Ashoke Sinha, San Bruno, both of Calif.

[73] Assignee: Idetek, Inc., San Bruno, Calif.

[21] Appl. No.: 138,305

[22] Filed: Dec. 28, 1987

[51] Int. Cl.$^4$ .................. G01N 33/53; G01N 33/543; C12Q 1/34; C12Q 1/26
[52] U.S. Cl. .......................................... 435/7; 435/18; 435/25; 435/810; 436/518; 436/815; 436/822; 436/809; 436/810
[58] Field of Search ....................... 435/7, 18, 25, 810; 436/518, 815, 822, 809, 810

[56] References Cited

U.S. PATENT DOCUMENTS 4,610,877  9/1986  Pearson et al. ...................... 424/88

*Primary Examiner*—Esther M. Kepplinger
*Assistant Examiner*—Toni R. Scheiner
*Attorney, Agent, or Firm*—Richard Neeley

[57] ABSTRACT

A method for detecting boar taint in a pig sample is provided. Anti-skatole antibodies are combined in a reaction buffer with a pig sample to form a reaction mixture. After incubating, the amount of skatole-antibody complex formation is determined. In a particular embodiment, the method utilizes solid substrate-affixed antibodies in a competitive inhibition assay with an enzyme-labeled skatole analogue. Kits facilitating the method are also provided.

21 Claims, No Drawings

DETECTION OF SKATOLE FOR MEAT QUALITY

TECHNICAL FIELD

The present invention relates to methods for determining the quality of meat and in particular to an assay for detecting boar taint.

BACKGROUND

Boar-taint is a major economic problem for the pork industry. Although only about 5 to 10% of male pigs are affected, the taint, an offensive, fecal smell associated with poor meat tenderness and often a bitter taste, is not detected until the meat is cooked. Because pigs having the taint are not readily distinguishable from unaffected pigs, pork producers castrate all male pigs at an early age. That procedure is costly and time consuming. Moreover, the castrated pigs suffer from retarded weight gain and decreased lean meat content. The process thus results in higher costs of pork production and hence higher cost for consumers.

Studies have shown that the contents of androstenone and skatole (3-methylindole) present in the carcass have a strong correlation to the unpleasant odor in the meat (Hansson et al., *Swedish J. Agric. Res.* (1980) 10:167–173; Walstra et al., *Res. Inst. for Animal Prod. "Schoonoord"*, Zeist, The Netherlands, "The androstenone-skatole as applied in a consumer test": and Mortensen and Sorensen *Proc. of the Danish Meat Res. Inst.*, "Relationship between boar taint and skatole determined with a new analysis method" (Apr. 5, 1984, Manuscript No. 661E). Indole, albeit in low concentration, is also reported to be present in boartaint (Hansson et al., supra). Evidence suggests that the skatole content of fat provides an estimate of the adverse odor, tenderness and overall taste for the meat (Mortensen et al., *Proc. of the Danish Meat Res. Inst.* (1986) 1:4,23–26). In particular, when the skatole content of the carcass body fat exceeds about 0.25 to 0.30 ppm, the pork has an offensive odor when cooked (Mortensen et al., supra).

At the present time, there is an analytical procedure that estimates skatole concentration in carcass fat by a colorimetric procedure (Mortensen and Sorensen, supra). The method is based on determining the concentration of a colored product produced when an indole derivative reacts with p-dimethylaminobenzaldehyde. The procedure is involved, utilizing a number of steps including grinding the sample, extracting skatole from fat with organic solvents, filtration and the colorimetric reaction. A major disadvantage of the method is that it does not provide the true skatole concentration, but rather indicates total indole derivatives present in the sample. Although skatole is expected to constitute a large percentage of the indole derivatives present, tryptophan, an amino acid present in proteins, is also detected by the assay method. Chromatographic analyses on the extracts have also been reported. See Garcia-Regueiro et al., *J. High Resolution Chromat. & Chromat. Comm.* (1986) 9:362–363.

A rapid, easy to perform assay that accurately determines tainted pigs would allow producers to discard affected carcasses at slaughter rather than castrate all boars at an early age.

Relevant Literature

Hansson et al., *Swedish J. Agric. Res.* (1980) 10:167–173 and Walstra et al., *Res. Inst. for Animal Prod. "Schoonoord"*, Zeist, The Netherlands, "The androstenone-skatole as applied in a consumer test" report that boar taint correlates with ansdrostenone and skatole. Mortensen and Sorensen, *Proc. of the Danish Meat Res. Inst.*, "Relationship between boar taint and skatole determined with a new analysis method" (Apr. 5, 1984) Manuscript No. 661E describe a colorimetric analysis for the determination of skatole in extracts of adipose tissue. Mortensen et al., *Proc. of the Danish Meat Res. Inst.* (1986) 1:4,23–26 report backfat skatole concentrations correlated with boat taint.

SUMMARY OF THE INVENTION

An immunochemical method for detecting boar taint is provided. Anti-skatole antibodies are combined in a reaction buffer with a pig sample to form a reaction mixture. After incubating, the amount of skatole-antibody complex formation is determined. In a particular embodiment, the method utilizes solid substrate-affixed antibodies in a competitive inhibition assay with an enzyme-labeled skatole analogue. Kits facilitating the method are also provided.

DETAILED DESCRIPTION OF THE SPECIFIC EMBODIMENTS

It has now been found that the concentration of skatole in pig samples which correlates with boar taint can be determined by a novel immunoassay. Any conventional immunoassay format can adapted to detection of skatole and used to determine boar taint in a pig carcass.

An immunoassay for determining skatole in pigs is provided. The method comprises combining anti-skatole antibodies in a suitable reaction buffer with a pig bodily fluid or tissue extract to form a reaction mixture. The reaction mixture is incubated for a sufficient period of time for the antibodies to react with skatole present in the sample. The amount of binding of the antibodies is determined as an indication of the concentration of skatole in the sample. The assay is advantageous in that unlike the prior art method which detects any compound having an indole moiety, it does not detect tryptophan.

The sample can be an aliquot of extracted fat or a pig bodily fluid such as blood. As stated previously, skatole must be extracted from pig fat, usually backfat, prior to assay. The sample is in an aqueous medium suitable for immunoassay. That is, the sample must not alter the assay reaction mixture to interfere with antibody-antigen binding or detection of the label. Blood samples are aqueous samples. Extracted fat samples must be placed in suitable media for immunoassays. By aqueous sample, it is meant that the sample is in a substantilly aqueous medium compatible with the reaction mixture in the concentration added. Conveniently, the subject assay is performed on pig blood, usually serum or plasma, which needs no special preparation prior to assay.

Either polyclonal or monoclonal anti-skatole antibodies may be suitable for use in the assay. The antibodies are prepared by conventional techniques. In particular, skatole or skatole analogues, such as immunologically cross-reactive indole derivatives, are haptens which can be conjugated to an immunogenic protein and used to induce antibodies in an appropriate host. Exemplary methods for preparation of skatole analogue conjugates and induced antibodies is described in detail in the experimental section.

The antibodies bind specifically to skatole. Antibody binding usually detects at least 80%, more usually at least about 90% of the skatole present in a pig sample having a skatole concentration (following dilution of the sample which may be used in a particular assay format) in the range of less than about 100 ppm, usually between about 0.01 and about 50 ppm, more usually between about 0.1 and 5.0 ppm. The antibodies are substantially free from reaction with tryptophan (2-amino-3-(3'-indolyl)propanoic acid) which frequently is also present in the sample and is unrelated to boar taint. By anti-skatole antibodies is meant an antibody that specifically binds skatole and is substantially free from binding to tryptophan.

Anti-skatole antibodies usually also bind to immunologically cross-reactive indole derivatives (skatole analogues) such as indole, 3-carboxymethylindole, and 3-[2-carboxyethyl]indole. By immunologically cross-reactive, it is meant that the skatole analogue is bound by anti-skatole antibodies. Therefore, usually, antibodies that bind to the skatole analogue also bind to skatole, and thus the skatole analogue can be used to induce anti-skatole antibodies. The sensitivity of the assay can be adjusted by using one skatole analogue to induce antibodies and another in the assay to compete for antibody binding with skatole in the sample. Usually the side group on the skatole analogue will differ from skatole by 1 to 10, usually 1 to 5, carbons and the analogue used to induce antibody will differ from the analogue used in the assay by no more than 5, usually no more than 3 carbons. Skatole analogues that induce anti-skatole antibodies and are useful as enzyme-conjugates to provide sensitive assays are described in the experimental section.

Numerous assay formats and protocols are taught in the prior art which may be employed in the subject invention. The formats of those assays, particularly with blood or serum samples, may be. readily adapted to the detection of skatole. The assays are usually performed in saline or buffered saline solutions such as phosphate buffered saline (PBS) or tris-buffered saline (TBS). Binding between the antibody and analyte is usually detected by use of a label. The label can have wide variations. It can be a radioisotope, a fluorophore, a free radical, cofactor, a metal, or usually an enzyme. The assay may be "homogeneous" (U.S. Pat. No. 3,817,837) e.g. EMIT, or "heterogeneous", e.g. ELISA (see, for example, U.S. Pat. No. 3,791,932.).

In heterogeneous immunoassays, either the analyte or the antibody, conveniently the antibody, may be affixed to a solid substrate. Usually the method will be based on competitive inhibition in a heterogeneous mode where a known amount of labeled skatole or, conveniently, a labeled skatole analogue, is added to the reaction mixture together with the sample to compete for substrate-affixed antibody. Unbound label can be separated from bound label by washing the solid substrate prior to determining the amount of complex. The amount of label bound to the substrate is inversely proportional to the amount of analyte in the sample. A standard curve can be prepared using known amounts of skatole as a control to determine the skatole concentration in a sample, and, thus, whether the carcass has boar taint.

As a first step of an embodiment of the method based on competitive inhibition, an aqueous sample from a pig is combined in a reaction buffer with labeled skatole or, usually, a labeled skatole analogue, and anti-skatole antibodies affixed to a solid substrate, conveniently a microtiter plate, to form a reaction mixture. The skatole analogue is conveniently labeled with an enzyme, most usually a hydrolase or an oxidoreductase. Well known enzyme labels include alkaline phosphatase, glucose oxidase, $\beta$-galactosidase, and peroxidase. Those enzymes and their substrates are available commercially from a number of sources. The concentration of the enzyme-conjugate is determined by the dynamic range of the skatole which may be present in the sample. The concentration will usually be in the same concentration range as the sample, with the conjugate usually present in excess.

The reaction mixture is incubated for a period of time sufficient to form an antibody-skatole complex with any skatole present in the reaction mixture. The incubation can be at a temperature in the range of above 0° C. to less than about 40° C., usually between about 4° C. and about 37° C., for a time period of about one half hour to an hour for temperatures of about 25° C. to about 37° C. and for about 2 to 4 hrs. or more at temperatures of about 4° C. Following the incubation, the solid substrate is washed. Usually the substrate is washed repeatedly with saline or a buffered saline. The wash buffer may include a detergent such as a nonionic detergent, for example polyoxylenesorbitan. The detergent will usually be present in a concentration of less than about 1%, more usually between about 0.01% to 0.1% (w/w).

The label is then detected by standard methods. When using an enzyme label, the detection comprises adding an enzyme substrate solution to the solid substrate to form a second reaction mixture. The second reaction mixture is incubated for a period of time sufficient for production of detectable substrate digestion product. Usually the incubation is at a temperature in the range of about 20° to about 40° C., most usually about 37° C. for a period of time between about 15 min. to about an hour, depending on the amount of enzyme present in the reaction mixture. Usually about 30 min. at about 37° C. is sufficient. Conveniently, following the incubation, the enzyme activity is stopped, usually by altering the pH of the reaction mixture a with sodium hydroxide.

The optical density of the reaction mixture is determined in comparison to the optical density of a sample having a known amount of skatole as an indication of boar taint in the pig. A pig is determined to have boar taint when a backfat sample has greater than about 0.3 ppm indole or a blood or other sample has a concentration which corresponds to 0.3 ppm skatole in backfat. To determine the corresponding concentration in blood, a number of backfat samples having normal skatole concentrations, indicating no boar taint, and a number of backfat samples having elevated skatole concentrations, indicating boar taint, are determined. A serum sample from each pig is determined. The serum value distinguishing the two types of samples is determined by comparing the two groups of values.

Kits facilitating the invention are also provided. A kit comprises, in separate containers, a labeled skatole analogue in a suitable reaction buffer and anti-skatole antibodies. Usually the antibodies are affixed to a solid substrate, most usually a microtiter plate. When the skatole analogue is labeled with an enzyme, a third container having enzyme substrate solution can be included in the kit. The kit may additionally contain a skatole analogue to be used as a control, preferably skatole, in a separate container.

The following examples are offered by way of illustration and not by way of limitation.

EXPERIMENTAL

Preparation of Anti-Skatole Antibodies

Anti-skatole antibodies were prepared essentially in the same manner as described by Weiler, *Planta* (1981) 153:319–324 for preparing antibodies to detect a plant hormone, indole acetic acid. A skatole analogue-, indole-3-acetic acid (IAA), bovine serum albumin (BSA) conjugate was prepared by a mixed anhydride method. IAA (52.3 mg, 300 μmol) in 2 ml dimethylformamide (DMF) was treated with 75 μl tri-n-butyl amine and the solution was cooled to about −10° to −15° C. Forty μl of isobutylchlorocarbonate was added to that mixture, and the solution was stirred for about 10 min. That mixture was continually stirred while a total of 420 mg of BSA, dissolved in a mixture of 23 ml 50% DMF solution and 420 μl of 1N NaOH was slowly added. Following addition of the BSA, the solution was stirred at 0° C. for an hour. 100 μl of 1N NaOH was then added. The mixture was stirred for an additional four hours at 0° C. That mixture was dialyzed twice against 2 L of 10% DMF and then against water (4×1 L).

Preparation of Indole-3-Butyric Acid Antibodies

The indole-3-butyric acid (IBA) antibodies were prepared in the same fashion as for indole-3-acetic acid. IBA-bovine serum albumin conjugate (or IBA-KLH conjugate) was prepared by a mixed anhydride method. IBA (60 mg, 300 μmol) in 2 mL DMF was treated with 75 μl tri-n-butyl amine and cooled to about −10° to −15° C. 40 μl isobutylchlorocarbonate was added to that mixture and stirred for about 10 min. That mixture was stirred while slowly adding 420 mg of BSA (or 100 mg KLH), dissolved in a mixture of 23 ml 50% DMF in water containing 420 μl of 1N NaOH. The mixture was stirred at 0° C. for an additional hour. 100 μl of 1N NaOH was then added and the mixture was stirred for another four hours at 0° C. Each conjugate mixture was dialyzed twice against 2 L of 10% DMF and finally against water (4×2 L).

Randomly bred rabbits were immunized with a 1:1 emulsion of the conjugate (2 mg/ml of 0.2M PBS, pH=7.4) and Freund's complete adjuvant. Blood was collected 2 weeks after first injection and thereafter each month. Protease and free albumin were removed from sera. Sufficient saturated ammonium sulphate was added to the sera to form a 45% ammonium sulphate solution. After stirring for two hours, the solution was centrifuged at 1000xg for 2 min. The pellets were resuspended in 45% $(NH_4)_2SO_4$ solution and centrifuged. The second pellet was suspended in 0.1M PBS (pH=8), desalted on a Bio-Gel column, and lyophilized for storage.

Conjugation of Skatole Analogues with Alkaline Phosphatase Label

A skatole analogue, indole-3-acetic acid (IAA), conjugate with alkaline phosphatase (AP) label was prepared according to established procedures for preparing polyclonal antibody to assay IAA in plants (Weiler, *Planta* (1981) 153:319–324 and Sandberg et al., *Immunochemistry* (1985) 24:1439–1442). The acid (17.5 mg, 0.085 mmole) dissolved in 1 ml 50% DMF (pH adjusted to 5.5 by 1N HCl) was mixed with 26.5 mg ethyldimethylaminopropylcarbodiimide (EDAC) (0.14 mmole) dissolved in 0.5 ml 50% DMF solution. After stirring at room temperature for 20 min., 20.0 μl of that solution was added to 50 μl of alkaline phosphatase (1 mg/100 μl) in 100 μl of 50% aq. The final pH of the solution was adjusted to 6.5 and the solution was then gently stirred at 4° C. for 4 hrs. The remainder of the procedure was the same as described below for conjugation of a second skatole analogue, indole-3-butyric acid, with alkaline phosphatase.

Indole-3-butyric acid (IBA)(35.3 mg: 0.174 mmole) dissolved in 2.0 ml 50% aq. DMF, adjusted to pH 5.5 with 1N NaOH, was mixed with 53.0 mg of EDAC (0.28 mmole) dissolved in 1 ml of 50% aq. DMF and was stirred at room temperature for 15–20 min. Alkaline phosphatase (AP) (100 μl) (Sigma, 13.4 mg protein/ml) was dissolved in 200 μl of 50% aq. DMF. 15.0 μl of the indolebutyric acid and EDAC mixture was added to 15.0 μl of the enzyme solution. The pH of the enzyme solution was adjusted to 6.5 with additional butyric acid/EDAC mixture and incubated at 4° C. for 4.0 hrs. with occasional stirring. The reaction mixture was transferred to dialysis tubing and dialyzed against 10% DMF solution (24 hr., 1 L) and then for three days against tris-buffered saline (TBS) containing 0.1% azide to produce indole-3-butyric acid-alkaline phosphatase conjugate (IBA-AP).

Coating of Microtiter Plates with Anti-Skatole Antibodies

Polyclonal antibody (12 mg) induced by a skatole analogue, indoleacetic acid, dissolved in 200 ml 50mM sodium bicarbonate buffer (pH=9.6) was used for coating purposes. 200 μl of the solution was used in each well of polystyrene high binding microtiter plates (Nunc, Sweden). The plates were incubated at 4° C. overnight. The wells were then washed with saline-Tween (polyoxylenesorbitan) solution (0.875% saline, 0.05% Tween-20 and 0.02% $NaN_3$) three times (200 μl) and incubated at room temperature for one hour with 200 μl/well of 1% rabbit serum albumin. Following washing with saline-Tween solution the wells were treated with 200 μl of a stabilizing solution (1% aqueous polyvinyl alcohol solution containing 0.1% $NaN_3$) for one hour at room temperature. The stabilizing solution was decanted and the plates were air dried and stored at −20° C. until use.

Titration Curve of Skatole Using Anti-IAA Antibodies and IAA-AP Conjugates

Plates coated with anti-IAA antibodies as described above were used. A 200 μl 1:1 mixture of 10,000 times diluted (from a concentration of 1.2 mg enzyme/ml) IAA-AP conjugate (in TBS, pH=8.5) and skatole solution (in TBS or 10% porcine serum solution) was added to each well in duplicate. The plates were incubated for 3 hrs. at 4° C. and then washed with saline-Tween solution followed by color development with 200 μl/well 0.1% p-nitrophosphate (PNP) solution at 37° C. for 35 min. and then with 50.0 μl of 0.1N NaOH solution to stop enzyme activity. The intensity of color developed was read by a vertical path spectrophotometer at 410 nm. Percent binding of the IAA-AP conjugate was calculated by the equation described below.

Titration Curve Using Anti-IAA Antibodies and Indolebutyric Acid Conjugate

Microtiter plates (Nunc, Sweden) coated with anti-indoleacetic acid polyclonal antibodies (described above) were used. A mixture of 100 μl of the enzyme conjugate (Indole-3-butyric acid-AP conjugate, prepared as described above, and diluted 1:10,000 in TBS) and 100 μl of skatole solution (either in TBS or in 10% porcine serum solution) of a number of dilutions was added to wells in duplicate. The mixture was incubated for 3 hrs. at 4° C. and then washed with saline-Tween solution 3 times (200 μl volume). 200 μl of the substrate solution (1mg/ml in TBS) was added per well and incubated at 37° C. for an hour. The wells were then treated with approximately 50.0 μl of 1N NaOH/well to stop the reaction. Final absorbances were measured.

The following equation was used to calculate the % binding of Indole-3-butyric acid:

$$\% \text{ Binding} = \frac{B_S - B_{NSB}}{B_0 - B_{NSB}} \times 100$$

where $B_S$=Absorbance of sample or standard $B_{NSB}$=Absorbance of sample used for non-specific binding, normally a sample containing 100 μl of the conjugate + 100 μl of a solution containing 250,000 picomoles of skatole.

$B_0$=Absorbance of sample containing no skatole to cross react with the conjugate.

Recovery of Skatole

A skatole recovery determination was performed with three sets of samples. Assay samples were prepared by mixing two standards of different concentrations in 10% porcine serum. The percentage binding of the conjugate in the samples was measured by the competitive inhibition assay described above. The final determination of the skatole concentration in these samples were calculated by comparison with a standard curve. The recovery results were:

| Picomoles of Skatole Added | Picomoles of Skatole Calculated from Standard Curve | % Recovery |
|---|---|---|
| 20,000.00 | 17,738 | 88.69 |
| 30,000.00 | 28,506 | 95.02 |
| 50,000.00 | 51,700 | 103.40 |

It is evident from the results described above that the present invention provides an accurate assay of the skatole content of a pig carcass sample which does not suffer from the disadvantages of previously used assays in quantitating all indole derivatives present in the sample. Thus, the assay method is substantially free from interference by tryptophan present in the sample. Additionally, the ability to use a pig blood sample eliminates the need to extract skatole from fat and simplifies the assay procedure.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for detecting boar taint in a pig comprising:
    (a) combining in a reaction buffer a sample from said pig and anti-skatole antibodies to form a reaction mixture;
    (b) incubating said reaction mixture for a period of time sufficient to form an antibody-skatole complex with any skatole present in said reaction mixture; and
    (c) determining the amount of antibody-skatole complex as an indication of boar taint in said pig.

2. The method of claim 1 wherein said sample comprises a member selected from the group consisting of whole blood, serum and plasma.

3. The method of claim 1 wherein said sample comprises backfat extract.

4. The method of claim 1 wherein said antibodies are affixed to a solid support.

5. The method of claim 4 wherein a known amount of labeled skatole or a labeled skatole analogue is added to said reaction mixture together with said sample and said determining comprises detecting the amount of label bound to said solid support.

6. The method of claim 1 wherein said sample is reacted with a known amount of said anti-skatole antibodies for a time sufficient to form an antibody-skatole complex with any skatole present in said sample to form a reaction mixture, said reaction mixture is incubated with solid support affixed skatole or a solid support-affixed skatole analogue and the amount of antibodies either bound to the support or in said reaction mixture is determined.

7. A method for detecting boar taint in a pig comprising:
    (a) combining in a reaction buffer a blood sample from said pig and anti-skatole antibodies affixed to a solid support to form a reaction mixture;
    (b) incubating said reaction mixture for a period of time sufficient to form an antibody-skatole complex with any skatole present in said reaction mixture;
    (c) washing said solid support; and
    (d) determining the amount of antibody-skatole complex affixed to said solid support as an indication of boar taint in said sample.

8. A method for detecting boar taint in a pig comprising:
    (a) combining in a reaction buffer a labeled skatole analogue, a blood sample from said pig and anti-skatole antibodies affixed to a solid support to form a reaction mixture;
    (b) incubating said reaction mixture for a period of time sufficient to form an antibody-skatole complex with any skatole present in said reaction mixture;
    (c) washing said solid support; and
    (d) determining the amount of said label bound to said solid support in comparison to a sample having a known amount of skatole as an indication of boar taint in said pig.

9. The method of claim 8 wherein said label is an enzyme.

10. The method of claim 9 wherein said enzyme is a hydrolase.

11. The method of claim 9 wherein said enzyme is an oxidoreductase.

12. The method of claim 8 wherein said skatole or skatole analogue is indole-3-butyric acid, 3-carboxymethylindole or 3-methylindole.

13. The method of claim 12, wherein said labeled skatole analogue is an indol-3-butyric acid/alkaline phosphatase conjugate.

14. The method of claim 8, wherein said labeled skatole analogue is a skatole analogue/enzyme conjugate and said determining of step (d) comprises:
   (i) adding a substrate for said enzyme to said solid support to form a second reaction mixture;
   (ii) incubating said second reaction mixture for a time period sufficient for production of detectable substrate digestion product; and
   (iii) measuring the optical density of said second reaction mixture.

15. A method for detecting boar taint in a pig comprising:
   (a) combining in a reaction buffer a conjugate of an enzyme with skatole or a skatole analogue, a blood sample from said pig, and anti-skatole antibodies affixed to a solid support to form a first reaction mixture;
   (b) incubating said first reaction mixture for a time period sufficient to form an antibody-skatole complex;
   (c) washing said solid support with a wash buffer;
   (d) incubating a solution containing a substrate for said enzyme with said solid support to form a second reaction mixture; and
   (e) determining the optical density of said second reaction mixture in comparison to the optical density of sample having a known amount of skatole as an indication of boar taint in said pig.

16. A method for detecting boar taint in a pig comprising:
   (a) combining a blood sample from said pig, indole-3-butyric acid/alkaline phosphatase conjugate in Tris-buffered saline, and anti-skatole antibodies affixed to a microtiter plate to form a first reaction mixture;
   (b) incubating said reaction mixture at about 4° C. for about four hours;
   (c) washing said microtiter plate with salinepolyoxylenesorbitan buffer;
   (d) incubating a p-nitrophenylphosphate solution with said microtiter plate at about 37° C. for about one hour to form a second reaction mixture:
   (e) altering the pH of said second reaction mixture to stop enzyme activity to form a third reaction mixture; and
   (f) determining the optical density of said third reaction mixture in comparison to the optical density of a sample having a known amount of skatole to determine the skatole concentration of said sample, wherein said pig is identified as having boar taint said sample has greater than about 0.3 ppm skatole.

17. The method of claim 16 wherein said pig blood sample comprises a member selected from the group consisting of serum and plasma.

18. A kit for determining boar taint in a pig blood sample comprising in separate containers (a) anti-skatole antibodies and (b) labeled skatole or a labeled skatole analogue.

19. The kit of claim 18 wherein said anti-skatole antibodies are affixed to a microtiter plate.

20. The kit of claim 18 wherein said skatole or skatole analogue is labeled with an enzyme.

21. The kit of claim 19 additionally comprising in a separate container skatole.

* * * * *